US006881563B2

(12) United States Patent
Donoho et al.

(10) Patent No.: US 6,881,563 B2
(45) Date of Patent: Apr. 19, 2005

(54) HUMAN PROTEASES AND POLYNUCLEOTIDES ENCODING THE SAME

(75) Inventors: Gregory Donoho, The Woodlands, TX (US); John Scoville, Houston, TX (US); C. Alexander Turner, Jr., The Woodlands, TX (US); Glenn Friedrich, Houston, TX (US); Alejandro Abuin, The Woodlands, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/766,074

(22) Filed: Jan. 28, 2004

(65) Prior Publication Data

US 2004/0137502 A1 Jul. 15, 2004

Related U.S. Application Data

(62) Division of application No. 10/214,811, filed on Aug. 7, 2002, now Pat. No. 6,743,621, which is a continuation of application No. 09/780,016, filed on Feb. 9, 2001, now Pat. No. 6,509,456.
(60) Provisional application No. 60/181,924, filed on Feb. 11, 2000.

(51) Int. Cl.[7] .............................. C12N 9/48; C12N 9/00; C07H 21/04; C12Q 1/00; C12Q 1/68; C12P 21/04
(52) U.S. Cl. ......................... 435/212; 536/23.2; 435/4; 435/6; 435/69.1; 435/183
(58) Field of Search .......................... 435/212; 536/23.2

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,656,603 A | 8/1997 | Simmons |
| 5,700,637 A | 12/1997 | Southern |
| 5,744,305 A | 4/1998 | Fodor et al. |
| 5,869,336 A | 2/1999 | Meyer et al. |
| 5,877,397 A | 3/1999 | Lonberg et al. |
| 5,948,767 A | 9/1999 | Scheule et al. |
| 5,972,680 A | 10/1999 | Knowles et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| | | |
|---|---|---|
| WO | WO 99/11799 | 3/1999 |
| WO | WO 99/64576 | 12/1999 |

OTHER PUBLICATIONS

Marra et al.: uj15h03.y1 Sugano mouse kidney mkia Mus musculus cDNA clone IMAGE: 1908149 5' similar to SW:YEQ8_YEAST P40051 Hypothetical 58.0 KD Peptidase in ARG5, 6–ILV1 Intergenic Region; mRNA sequence: EMBL Sequence Database, Oct. 31, 1998, XP002171875.

Matthews, L: "Human DNA sequence from clone RP5–1057d18 on chromosome 22q13.33 Contains the gene for a novel protein similar to yeast and bacterial PEPP (aminopeptidase P, aminoacylproline aminopeptidase), ESTs and GSSs" EMBL Sequence Database, Feb. 24, 1999, XP002171876.

Collins et al.: "Novel human gene mapping to chromosome 22", EMBL Sequence Database, Jul. 12, 2000, XP002171877.

Collins et al.: "Hypothetical 58.0 kD protein" Swissprot Sequence Data Base, Oct. 1, 2000, XP002171878.

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

(Continued)

*Primary Examiner*—Rao Manjunath
*Assistant Examiner*—Yong D. Pak

(57) ABSTRACT

Novel human polynucleotide and polypeptide sequences are disclosed that can be used in therapeutic, diagnostic, and pharmacogenomic applications.

1 Claim, No Drawings

OTHER PUBLICATIONS

Inoue et al, 1987, "Synthesis and hybridization studies on two complementary nona(2'-O-methyl)ribonucleotides", Nucleic Acids Research 15(15):6131–6149.

Inouye & Inouye, 1985, "Up–promoter mutations in the Ipp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ripka, 1988, "Computers picture the perfect drug", New Scientist 16:54–57.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

SEQUENCE LISTING

<160> NUMBER OF SEQ ID NOS: 27

<210> SEQ ID NO 1
<211> LENGTH: 1524
<212> TYPE: DNA
<213> ORGANISM: homo sapiens

<400> SEQUENCE: 1

```
atgccttggc tgctctcagc ccccaagctg gttcccgctg tagcaaacgt ccgcggcctc      60
tcaggatgta tgttgtgttc acagcgaagg tactcccttc agcctgtccc agaaaggagg     120
attccaaacc gatacttagg ccagcccagc ccctttacac acccacacct cctcagacca     180
ggggaggtaa ctccaggact atctcaggtg gaatatgcac ttcgcagaca caaactaatg     240
tctctgatcc agaaggaagc tcaagggcag agtgggacag accagacagt ggttgtgctc     300
tccaacccta catactacat gagcaacgat attccctata ctttccacca agacaacaat     360
ttcctgtacc tatgtggatt ccaagagcct gatagcattc ttgtccttca gagcctccct     420
ggcaaacaat taccatcaca caaagccata cttttttgtgc ctcggcgaga tcccagtcga     480
gaactttggg atggtccgcg atctggcact gatggagcaa tagctctaac tggagtagac     540
gaagcctata cgctagaaga atttcaacat cttctaccaa aaatgaaagc tgagacgaac     600
atggtttggt atgactggat gaggccctca catgcacagc ttcactctga ctatatgcag     660
cccctgactg aggccaaagc caagagcaag aacaaggttc ggggtgttca gcagctgata     720
cagcgcctcc ggctgatcaa gtctcctgca gaaattgaac gaatgcagat tgctgggaag     780
ctgacatcac aggctttcat agaaaccatg ttcaccagta aagcccctgt ggaagaagcc     840
tttctttatg ctaagtttga atttgaatgc cgggctcgtg gcgcagacat tttagcctat     900
ccacctgtgg tggctggtgg taatcggtca aacactttgc actatgtgaa aaataatcaa     960
ctcatcaagg atggggaaat ggtgcttctg gatggaggtt gtgagtcttc ctgctatgtg    1020
agtgacatca cacgtacgtg gccagtcaat ggcaggttca ccgcacctca ggcagaactc    1080
tatgaagccg ttctagagat ccaaagagat tgtttggccc tctgcttccc tgggacaagc    1140
ttggagaaca tctacagcat gatgctgacc ctgataggac agaagcttaa agacttgggg    1200
atcatgaaga acattaagga aaataatgcc ttcaaggctg ctcgaaaata ctgtcctcat    1260
catgttggcc actacctcgg gatggatgtc catgacactc cagacatgcc ccgttccctc    1320
cctctgcagc ctgggatggt aatcacaatt gagcccggca tttatattcc agaggatgac    1380
aaagatgccc cagagaagtt tcggggtctt ggtgtacgaa ttgaggatga tgtagtggtg    1440
actcaggact cacctctcat cctttctgca gactgtccca aagagatgaa tgacattgaa    1500
cagatatgca gccaggcttc ttga                                          1524
```

<210> SEQ ID NO 2
<211> LENGTH: 507
<212> TYPE: PRT
<213> ORGANISM: homo sapiens -continued

<400> SEQUENCE: 2

```
Met Pro Trp Leu Leu Ser Ala Pro Lys Leu Val Pro Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Ala Glu Thr Asn Met Val Trp Tyr Asp Trp Met Arg
        195                 200                 205

Pro Ser His Ala Gln Leu His Ser Asp Tyr Met Gln Pro Leu Thr Glu
    210                 215                 220

Ala Lys Ala Lys Ser Lys Asn Lys Val Arg Gly Val Gln Gln Leu Ile
225                 230                 235                 240

Gln Arg Leu Arg Leu Ile Lys Ser Pro Ala Glu Ile Glu Arg Met Gln
                245                 250                 255

Ile Ala Gly Lys Leu Thr Ser Gln Ala Phe Ile Glu Thr Met Phe Thr
            260                 265                 270

Ser Lys Ala Pro Val Glu Glu Ala Phe Leu Tyr Ala Lys Phe Glu Phe
        275                 280                 285

Glu Cys Arg Ala Arg Gly Ala Asp Ile Leu Ala Tyr Pro Pro Val Val
    290                 295                 300

Ala Gly Gly Asn Arg Ser Asn Thr Leu His Tyr Val Lys Asn Asn Gln
305                 310                 315                 320

Leu Ile Lys Asp Gly Glu Met Val Leu Leu Asp Gly Gly Cys Glu Ser
                325                 330                 335

Ser Cys Tyr Val Ser Asp Ile Thr Arg Thr Trp Pro Val Asn Gly Arg
            340                 345                 350

Phe Thr Ala Pro Gln Ala Glu Leu Tyr Glu Ala Val Leu Glu Ile Gln
        355                 360                 365

Arg Asp Cys Leu Ala Leu Cys Phe Pro Gly Thr Ser Leu Glu Asn Ile
    370                 375                 380

Tyr Ser Met Met Leu Thr Leu Ile Gly Gln Lys Leu Lys Asp Leu Gly
385                 390                 395                 400

Ile Met Lys Asn Ile Lys Glu Asn Asn Ala Phe Lys Ala Ala Arg Lys
                405                 410                 415
```

```
Tyr Cys Pro His His Val Gly His Tyr Leu Gly Met Asp Val His Asp
            420                 425                 430

Thr Pro Asp Met Pro Arg Ser Leu Pro Leu Gln Pro Gly Met Val Ile
        435                 440                 445

Thr Ile Glu Pro Gly Ile Tyr Ile Pro Glu Asp Asp Lys Asp Ala Pro
    450                 455                 460

Glu Lys Phe Arg Gly Leu Gly Val Arg Ile Glu Asp Asp Val Val Val
465                 470                 475                 480

Thr Gln Asp Ser Pro Leu Ile Leu Ser Ala Asp Cys Pro Lys Glu Met
                485                 490                 495

Asn Asp Ile Glu Gln Ile Cys Ser Gln Ala Ser
            500                 505

<210> SEQ ID NO 3
<211> LENGTH: 210
<212> TYPE: DNA
<213> ORGANISM: homo sapiens

<400> SEQUENCE: 3
atgccttggc tgctctcagc ccccaagctg gttcccgctg tagcaaacgt ccgcggcctc      60
tcaggatgta tgttgtgttc acagcgaagg tactcccttc agcctgtccc agaaaggagg     120
attccaaacc gatacttagg ccagcccagc ccctttacac acccacacct cctcagacca     180
gactcgaatt cctgctggga agtcggctga                                      210

<210> SEQ ID NO 4
<211> LENGTH: 69
<212> TYPE: PRT
<213> ORGANISM: homo sapiens

<400> SEQUENCE: 4

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Asp Ser Asn Ser
    50                  55                  60

Cys Trp Glu Val Gly
65

<210> SEQ ID NO 5
<211> LENGTH: 873
<212> TYPE: DNA
<213> ORGANISM: homo sapiens

<400> SEQUENCE: 5
atgccttggc tgctctcagc ccccaagctg gttcccgctg tagcaaacgt ccgcggcctc      60
tcaggatgta tgttgtgttc acagcgaagg tactcccttc agcctgtccc agaaaggagg     120
attccaaacc gatacttagg ccagcccagc ccctttacac acccacacct cctcagacca     180
ggggaggtaa ctccaggact atctcaggtg aatatgcac ttcgcagaca caaactaatg      240
tctctgatcc agaaggaagc tcaagggcag agtgggacag accagacagt ggttgtgctc     300
tccaacccta catactacat gagcaacgat attcccctata cttttccacca agacaacaat    360 ttcctgtacc tatgtggatt ccaagagcct gatagcattc ttgtccttca gagcctccct     420
```

```
ggcaaacaat taccatcaca caaagccata cttttttgtgc ctcggcgaga tcccagtcga    480
gaactttggg atggtccgcg atctggcact gatggagcaa tagctctaac tggagtagac    540
gaagcctata cgctagaaga atttcaacat cttctaccaa aaatgaaagt gctcttgcca    600
gctcttcaaa aggaggtact gttctccaag aacgatccat gcatcacagc atcagaatca    660
cctgctgaga cgaacatggt ttggtatgac tggatgaggc cctcacatgc acagcttcac    720
tctgactata tgcagcccct gactgaggcc aaagccaaga gcaagaacaa ggttcggggt    780
gttcagcagc tgatacagcg cctccggctg atcaagtctc ctgcagaaat tgaacgaatg    840
cagattgctg ggaagctgac atcacaggta tga                                 873
```

<210> SEQ ID NO 6
<211> LENGTH: 290
<212> TYPE: PRT
<213> ORGANISM: homo sapiens

<400> SEQUENCE: 6

```
Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Val Leu Leu Pro Ala Leu Gln Lys Glu Val Leu Phe
        195                 200                 205

Ser Lys Asn Asp Pro Cys Ile Thr Ala Ser Glu Ser Pro Ala Glu Thr
    210                 215                 220

Asn Met Val Trp Tyr Asp Trp Met Arg Pro Ser His Ala Gln Leu His
225                 230                 235                 240

Ser Asp Tyr Met Gln Pro Leu Thr Glu Ala Lys Ala Lys Ser Lys Asn
                245                 250                 255

Lys Val Arg Gly Val Gln Gln Leu Ile Gln Arg Leu Arg Leu Ile Lys
            260                 265                 270

Ser Pro Ala Glu Ile Glu Arg Met Gln Ile Ala Gly Lys Leu Thr Ser
        275                 280                 285
```

Gln Val
    290

<210> SEQ ID NO 7
<211> LENGTH: 798
<212> TYPE: DNA
<213> ORGANISM: homo sapiens

<400> SEQUENCE: 7

```
atgccttggc tgctctcagc ccccaagctg gttcccgctg tagcaaacgt ccgcggcctc      60
tcaggatgta tgttgtgttc acagcgaagg tactcccttc agcctgtccc agaaaggagg     120
attccaaacc gatacttagg ccagcccagc ccctttacac acccacacct cctcagacca     180
ggggaggtaa ctccaggact atctcaggtg aatatgcac  ttcgcagaca caaactaatg     240
tctctgatcc agaaggaagc tcaagggcag agtgggacag accagacagt ggttgtgctc     300
tccaacccta catactacat gagcaacgat attccctata ctttccacca agacaacaat     360
ttcctgtacc tatgtggatt ccaagagcct gatagcattc ttgtccttca gagcctccct     420
ggcaaacaat taccatcaca caaagccata cttttttgtgc ctcggcgaga tcccagtcga     480
gaactttggg atggtccgcg atctggcact gatggagcaa tagctctaac tggagtagac     540
gaagcctata cgctagaaga atttcaacat cttctaccaa aaatgaaagc tgagacgaac     600
atggtttggt atgactggat gaggcccctca catgcacagc ttcactctga ctatatgcag     660
cccctgactg aggccaaagc caagagcaag aacaaggttc ggggtgttca gcagctgata     720
cagcgcctcc ggctgatcaa gtctcctgca gaaattgaac gaatgcagat tgctgggaag     780
ctgacatcac aggtatga                                                   798
```

<210> SEQ ID NO 8
<211> LENGTH: 265
<212> TYPE: PRT
<213> ORGANISM: homo sapiens

<400> SEQUENCE: 8

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

```
Thr Gly Val Asp Glu Ala Tyr Thr Leu Glu Glu Phe Gln His Leu Leu
            180                 185                 190

Pro Lys Met Lys Ala Glu Thr Asn Met Val Trp Tyr Asp Trp Met Arg
        195                 200                 205

Pro Ser His Ala Gln Leu His Ser Asp Tyr Met Gln Pro Leu Thr Glu
        210                 215                 220

Ala Lys Ala Lys Ser Lys Asn Lys Val Arg Gly Val Gln Gln Leu Ile
225                 230                 235                 240

Gln Arg Leu Arg Leu Ile Lys Ser Pro Ala Glu Ile Glu Arg Met Gln
            245                 250                 255

Ile Ala Gly Lys Leu Thr Ser Gln Val
            260                 265

<210> SEQ ID NO 9
<211> LENGTH: 636
<212> TYPE: DNA
<213> ORGANISM: homo sapiens

<400> SEQUENCE: 9
atgtctctga tccagaagga agctcaaggg cagagtggga cagaccagac agtggttgtg     60
ctctccaacc ctacatacta catgagcaac gatattccct atactttcca ccaagacaac    120
aatttcctgt acctatgtgg attccaagag cctgatagca ttcttgtcct tcagagcctc    180
cctggcaaac aattaccatc acacaaagcc atactttttg tgcctcggcg agatcccagt    240
cgagaacttt gggatggtcc gcgatctggc actgatggac aatagctct aactggagta    300 gacgaagcct atacgctaga gaatttcaa catcttctac caaaaatgaa agtgctcttg    360
ccagctcttc aaaaggaggt actgttctcc aagaacgatc catgcatcac agcatcagaa    420
tcacctgctg agacgaacat ggtttggtat gactggatga ggccctcaca tgcacagctt    480
cactctgact atatgcagcc cctgactgag gccaaagcca agagcaagaa caaggttcgg    540
ggtgttcagc agctgataca gcgcctccgg ctgatcaagt ctcctgcaga aattgaacga    600
atgcagattg ctgggaagct gacatcacag gtatga                             636

<210> SEQ ID NO 10
<211> LENGTH: 211
<212> TYPE: PRT
<213> ORGANISM: homo sapiens

<400> SEQUENCE: 10

Met Ser Leu Ile Gln Lys Glu Ala Gln Gly Gln Ser Gly Thr Asp Gln
1               5                   10                  15

Thr Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
            35                  40                  45

Gln Glu Pro Asp Ser Ile Leu Val Leu Gln Ser Leu Pro Gly Lys Gln
        50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
            85                  90                  95

Leu Thr Gly Val Asp Glu Ala Tyr Thr Leu Glu Glu Phe Gln His Leu
            100                 105                 110

Leu Pro Lys Met Lys Val Leu Leu Pro Ala Leu Gln Lys Glu Val Leu
```

-continued

```
                115                 120                 125
Phe Ser Lys Asn Asp Pro Cys Ile Thr Ala Ser Glu Ser Pro Ala Glu
        130                 135                 140

Thr Asn Met Val Trp Tyr Asp Trp Met Arg Pro Ser His Ala Gln Leu
145                 150                 155                 160

His Ser Asp Tyr Met Gln Pro Leu Thr Glu Ala Lys Ala Lys Ser Lys
                165                 170                 175

Asn Lys Val Arg Gly Val Gln Gln Leu Ile Gln Arg Leu Arg Leu Ile
            180                 185                 190

Lys Ser Pro Ala Glu Ile Glu Arg Met Gln Ile Ala Gly Lys Leu Thr
        195                 200                 205

Ser Gln Val
    210
```

<210> SEQ ID NO 11
<211> LENGTH: 804
<212> TYPE: DNA
<213> ORGANISM: homo sapiens

<400> SEQUENCE: 11

```
atgttgtgtt cacagcgaag gtactccctt cagcctgtcc cagaaaggag gattccaaac    60
cgatacttag gccagcccag ccccttaca  cacccacacc tcctcagacc agggagggta   120
actccaggac tatctcaggt ggaatatgca cttcgcagac acaaactaat gtctctgatc   180
cagaaggaag ctcaagggca gagtgggaca gaccagacag tggttgtgct ctccaaccct   240
acatactaca tgagcaacga tattccctat actttccacc aagacaacaa tttcctgtac   300
ctatgtggat ccaagagcc  tgatagcatt cttgtccttc agagcctccc tggcaaacaa   360
ttaccatcac acaaagccat acttttttgtg cctcggcgag atcccagtcg agaactttgg   420
gatggtccgc gatctggcac tgatggagca atagctctaa ctggagtaga cgaagcctat   480
acgctagaag aatttcaaca tcttctacca aaaatgaaag tgctcttgcc agctcttcaa   540
aaggaggtac tgttctccaa gaacgatcca tgcatcacag catcagaatc acctgctgag   600
acgaacatgg tttggtatga ctggatgagg ccctcacatg cacagcttca ctctgactat   660
atgcagcccc tgactgaggc caaagccaag agcaagaaca aggttcgggg tgttcagcag   720
ctgatacagc gcctccggct gatcaagtct cctgcagaaa ttgaacgaat gcagattgct   780
gggaagctga catcacaggt atga                                          804
```

<210> SEQ ID NO 12
<211> LENGTH: 267
<212> TYPE: PRT
<213> ORGANISM: homo sapiens

<400> SEQUENCE: 12

```
Met Leu Cys Ser Gln Arg Arg Tyr Ser Leu Gln Pro Val Pro Glu Arg
  1               5                  10                  15

Arg Ile Pro Asn Arg Tyr Leu Gly Gln Pro Ser Pro Phe Thr His Pro
              20                  25                  30

His Leu Leu Arg Pro Gly Glu Val Thr Pro Gly Leu Ser Gln Val Glu
          35                  40                  45

Tyr Ala Leu Arg Arg His Lys Leu Met Ser Leu Ile Gln Lys Glu Ala
      50                  55                  60

Gln Gly Gln Ser Gly Thr Asp Gln Thr Val Val Val Leu Ser Asn Pro
65                  70                  75                  80
```

```
Thr Tyr Tyr Met Ser Asn Asp Ile Pro Tyr Thr Phe His Gln Asp Asn
                85                  90                  95

Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125

Phe Val Pro Arg Arg Asp Pro Ser Arg Glu Leu Trp Asp Gly Pro Arg
    130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Val Leu Leu
                165                 170                 175

Pro Ala Leu Gln Lys Glu Val Leu Phe Ser Lys Asn Asp Pro Cys Ile
            180                 185                 190

Thr Ala Ser Glu Ser Pro Ala Glu Thr Asn Met Val Trp Tyr Asp Trp
        195                 200                 205

Met Arg Pro Ser His Ala Gln Leu His Ser Asp Tyr Met Gln Pro Leu
    210                 215                 220

Thr Glu Ala Lys Ala Lys Ser Lys Asn Lys Val Arg Gly Val Gln Gln
225                 230                 235                 240

Leu Ile Gln Arg Leu Arg Leu Ile Lys Ser Pro Ala Glu Ile Glu Arg
                245                 250                 255

Met Gln Ile Ala Gly Lys Leu Thr Ser Gln Val
            260                 265

<210> SEQ ID NO 13
<211> LENGTH: 561
<212> TYPE: DNA
<213> ORGANISM: homo sapiens

<400> SEQUENCE: 13
atgtctctga tccagaagga agctcaaggg cagagtggga cagaccagac agtggttgtg    60
ctctccaacc ctacatacta catgagcaac gatattccct atactttcca ccaagacaac   120
aatttcctgt acctatgtgg attccaagag cctgatagca ttcttgtcct tcagagcctc   180
cctggcaaac aattaccatc acacaaagcc atacttttg tgcctcggcg agatcccagt    240
cgagaacttt gggatggtcc gcgatctggc actgatggag caatagctct aactggagta   300
gacgaagcct atacgctaga agaatttcaa catcttctac aaaaatgaa agctgagacg    360 aacatggttt ggtatgactg gatgaggccc tcacatgcac agcttcactc tgactatatg   420
cagcccctga ctgaggccaa agccaagagc aagaacaagg ttcggggtgt tcagcagctg   480
atacagcgcc tccggctgat caagtctcct gcagaaattg aacgaatgca gattgctggg   540
aagctgacat cacaggtatg a                                            561

<210> SEQ ID NO 14
<211> LENGTH: 186
<212> TYPE: PRT
<213> ORGANISM: homo sapiens

<400> SEQUENCE: 14

Met Ser Leu Ile Gln Lys Glu Ala Gln Gly Gln Ser Gly Thr Asp Gln
1               5                   10                  15

Thr Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
```

```
                35                  40                  45
Gln Glu Pro Asp Ser Ile Leu Val Leu Gln Ser Leu Pro Gly Lys Gln
 50                  55                  60

Leu Pro Ser His Lys Ala Ile Leu Phe Val Pro Arg Arg Asp Pro Ser
 65                  70                  75                  80

Arg Glu Leu Trp Asp Gly Pro Arg Ser Gly Thr Asp Gly Ala Ile Ala
                 85                  90                  95

Leu Thr Gly Val Asp Glu Ala Tyr Thr Leu Glu Phe Gln His Leu
                100                 105                 110

Leu Pro Lys Met Lys Ala Glu Thr Asn Met Val Trp Tyr Asp Trp Met
            115                 120                 125

Arg Pro Ser His Ala Gln Leu His Ser Asp Tyr Met Gln Pro Leu Thr
        130                 135                 140

Glu Ala Lys Ala Lys Ser Lys Asn Lys Val Arg Gly Val Gln Gln Leu
145                 150                 155                 160

Ile Gln Arg Leu Arg Leu Ile Lys Ser Pro Ala Glu Ile Glu Arg Met
                165                 170                 175

Gln Ile Ala Gly Lys Leu Thr Ser Gln Val
            180                 185
```

<210> SEQ ID NO 15
<211> LENGTH: 729
<212> TYPE: DNA
<213> ORGANISM: homo sapiens

<400> SEQUENCE: 15

```
atgttgtgtt cacagcgaag gtactccctt cagcctgtcc cagaaggag gattccaaac     60
cgatacttag gccagcccag ccccttaca cacccacacc tcctcagacc aggggaggta   120
actccaggac tatctcaggt ggaatatgca cttcgcagac acaaactaat gtctctgatc   180
cagaaggaag ctcaagggca gagtgggaca gaccagacag tggttgtgct ctccaaccct   240
acatactaca tgagcaacga tattccctat actttccacc aagacaacaa tttcctgtac   300
ctatgtggat ccaagagcc tgatagcatt cttgtcctc agagcctccc tggcaaacaa   360
ttaccatcac acaaagccat acttttgtg cctcggcgag atcccagtcg agaactttgg   420
gatggtccgc gatctggcac tgatggagca atagctctaa ctggagtaga cgaagcctat   480
acgctagaag aatttcaaca tcttctacca aaaatgaaag ctgagacgaa catggtttgg   540
tatgactgga tgaggccctc acatgcacag cttcactctg actatatgca gcccctgact   600
gaggccaaag ccaagagcaa gaacaaggtt cggggtgttc agcagctgat acagcgcctc   660
cggctgatca gtctcctgc agaaattgaa cgaatgcaga ttgctgggaa gctgacatca   720
caggtatga                                                         729
```

<210> SEQ ID NO 16
<211> LENGTH: 242
<212> TYPE: PRT
<213> ORGANISM: homo sapiens

<400> SEQUENCE: 16

```
Met Leu Cys Ser Gln Arg Arg Tyr Ser Leu Gln Pro Val Pro Glu Arg
 1               5                  10                  15

Arg Ile Pro Asn Arg Tyr Leu Gly Gln Pro Ser Pro Phe Thr His Pro
             20                  25                  30

His Leu Leu Arg Pro Gly Glu Val Thr Pro Gly Leu Ser Gln Val Glu
         35                  40                  45
```

```
Tyr Ala Leu Arg Arg His Lys Leu Met Ser Leu Ile Gln Lys Glu Ala
         50                  55                  60
Gln Gly Gln Ser Gly Thr Asp Gln Thr Val Val Leu Ser Asn Pro
 65                  70                  75                  80
Thr Tyr Tyr Met Ser Asn Asp Ile Pro Tyr Thr Phe His Gln Asp Asn
                 85                  90                  95
Asn Phe Leu Tyr Leu Cys Gly Phe Gln Glu Pro Asp Ser Ile Leu Val
             100                 105                 110
Leu Gln Ser Leu Pro Gly Lys Gln Leu Pro Ser His Lys Ala Ile Leu
             115                 120                 125
Phe Val Pro Arg Arg Asp Pro Ser Arg Glu Leu Trp Asp Gly Pro Arg
        130                 135                 140
Ser Gly Thr Asp Gly Ala Ile Ala Leu Thr Gly Val Asp Glu Ala Tyr
145                 150                 155                 160
Thr Leu Glu Glu Phe Gln His Leu Leu Pro Lys Met Lys Ala Glu Thr
                165                 170                 175
Asn Met Val Trp Tyr Asp Trp Met Arg Pro Ser His Ala Gln Leu His
            180                 185                 190
Ser Asp Tyr Met Gln Pro Leu Thr Glu Ala Lys Ala Lys Ser Lys Asn
            195                 200                 205
Lys Val Arg Gly Val Gln Gln Leu Ile Gln Arg Leu Arg Leu Ile Lys
        210                 215                 220
Ser Pro Ala Glu Ile Glu Arg Met Gln Ile Ala Gly Lys Leu Thr Ser
225                 230                 235                 240
Gln Val

<210> SEQ ID NO 17
<211> LENGTH: 1362
<212> TYPE: DNA
<213> ORGANISM: homo sapiens

<400> SEQUENCE: 17
atgtctctga tccagaagga agctcaaggg cagagtggga cagaccagac agtggttgtg      60
ctctccaacc ctacatacta catgagcaac gatattccct actttccca ccaagacaac     120
aatttcctgt acctatgtgg attccaagag cctgatagca ttcttgtcct tcagagcctc     180
cctggcaaac aattaccatc acacaaagcc atactttttg tgcctcggcg agatcccagt     240
cgagaacttt gggatggtcc gcgatctggc actgatggag caatagctct aactggagta     300
gacgaagcct atacgctaga agaatttcaa catcttctac aaaaatgaa agtgctcttg      360
ccagctcttc aaaaggaggt actgttctcc aagaacgatc catgcatcac agcatcagaa     420
tcacctgctg agacgaacat ggtttggtat gactggatga ggccctcaca tgcacagctt     480
cactctgact atatgcagcc cctgactgag gccaaagcca agagcaagaa caaggttcgg     540
ggtgttcagc agctgataca gcgcctccgg ctgatcaagt ctcctgcaga aattgaacga     600
atgcagattg ctgggaagct gacatcacag gctttcatag aaaccatgtt caccagtaaa     660
gcccctgtgg aagaagcctt tctttatgct aagtttgaat tgaatgccgg gctcgtggc      720
gcagacattt tagcctatcc acctgtggtg gctggtggta atcggtcaaa cacttttgcac    780
tatgtgaaaa ataatcaact catcaaggat ggggaaatgg tgcttctgga tggaggttgt     840
gagtcttcct gctatgtgag tgacatcaca cgtacgtggc cagtcaatgg caggttcacc     900
gcacctcagg cagaactcta tgaagccgtt ctagagatcc aaagagattg tttggccctc     960
```

-continued

```
tgcttccctg ggacaagctt ggagaacatc tacagcatga tgctgaccct gataggacag    1020
aagcttaaag acttggggat catgaagaac attaaggaaa ataatgcctt caaggctgct    1080
cgaaaatact gtcctcatca tgttggccac tacctcggga tggatgtcca tgacactcca    1140
gacatgcccc gttccctccc tctgcagcct gggatggtaa tcacaattga gcccggcatt    1200
tatattccag aggatgacaa agatgcccca gagaagtttc ggggtcttgg tgtacgaatt    1260
gaggatgatg tagtggtgac tcaggactca cctctcatcc tttctgcaga ctgtcccaaa    1320
gagatgaatg acattgaaca gatatgcagc caggcttctt ga                      1362
```

<210> SEQ ID NO 18
<211> LENGTH: 453
<212> TYPE: PRT
<213> ORGANISM: homo sapiens

<400> SEQUENCE: 18

```
Met Ser Leu Ile Gln Lys Glu Ala Gln Gly Gln Ser Gly Thr Asp Gln
 1               5                  10                  15

Thr Val Val Leu Ser Asn Pro Thr Tyr Tyr Met Ser Asn Asp Ile
                20                  25                  30

Pro Tyr Thr Phe His Gln Asp Asn Asn Phe Leu Tyr Leu Cys Gly Phe
                35                  40                  45

Gln Glu Pro Asp Ser Ile Leu Val Leu Gln Ser Leu Pro Gly Lys Gln
 50                  55                  60

Leu Pro Ser His Lys Ala Ile Leu Phe Val Pro Arg Arg Asp Pro Ser
 65                  70                  75                  80

Arg Glu Leu Trp Asp Gly Pro Arg Ser Gly Thr Asp Gly Ala Ile Ala
                85                  90                  95

Leu Thr Gly Val Asp Glu Ala Tyr Thr Leu Glu Glu Phe Gln His Leu
                100                 105                 110

Leu Pro Lys Met Lys Val Leu Leu Pro Ala Leu Gln Lys Glu Val Leu
                115                 120                 125

Phe Ser Lys Asn Asp Pro Cys Ile Thr Ala Ser Glu Ser Pro Ala Glu
 130                 135                 140

Thr Asn Met Val Trp Tyr Asp Trp Met Arg Pro Ser His Ala Gln Leu
145                 150                 155                 160

His Ser Asp Tyr Met Gln Pro Leu Thr Glu Ala Lys Ala Lys Ser Lys
                165                 170                 175

Asn Lys Val Arg Gly Val Gln Gln Leu Ile Gln Arg Leu Arg Leu Ile
                180                 185                 190

Lys Ser Pro Ala Glu Ile Glu Arg Met Gln Ile Ala Gly Lys Leu Thr
                195                 200                 205

Ser Gln Ala Phe Ile Glu Thr Met Phe Thr Ser Lys Ala Pro Val Glu
 210                 215                 220

Glu Ala Phe Leu Tyr Ala Lys Phe Glu Phe Glu Cys Arg Ala Arg Gly
225                 230                 235                 240

Ala Asp Ile Leu Ala Tyr Pro Pro Val Val Ala Gly Gly Asn Arg Ser
                245                 250                 255

Asn Thr Leu His Tyr Val Lys Asn Asn Gln Leu Ile Lys Asp Gly Glu
                260                 265                 270

Met Val Leu Leu Asp Gly Gly Cys Glu Ser Ser Cys Tyr Val Ser Asp
                275                 280                 285

Ile Thr Arg Thr Trp Pro Val Asn Gly Arg Phe Thr Ala Pro Gln Ala
                290                 295                 300
```

-continued

```
Glu Leu Tyr Glu Ala Val Leu Glu Ile Gln Arg Asp Cys Leu Ala Leu
305                 310                 315                 320

Cys Phe Pro Gly Thr Ser Leu Glu Asn Ile Tyr Ser Met Met Leu Thr
                325                 330                 335

Leu Ile Gly Gln Lys Leu Lys Asp Leu Gly Ile Met Lys Asn Ile Lys
            340                 345                 350

Glu Asn Asn Ala Phe Lys Ala Ala Arg Lys Tyr Cys Pro His His Val
        355                 360                 365

Gly His Tyr Leu Gly Met Asp Val His Asp Thr Pro Asp Met Pro Arg
    370                 375                 380

Ser Leu Pro Leu Gln Pro Gly Met Val Ile Thr Ile Glu Pro Gly Ile
385                 390                 395                 400

Tyr Ile Pro Glu Asp Asp Lys Asp Ala Pro Glu Lys Phe Arg Gly Leu
                405                 410                 415

Gly Val Arg Ile Glu Asp Asp Val Val Val Thr Gln Asp Ser Pro Leu
            420                 425                 430

Ile Leu Ser Ala Asp Cys Pro Lys Glu Met Asn Asp Ile Glu Gln Ile
        435                 440                 445

Cys Ser Gln Ala Ser
    450

<210> SEQ ID NO 19
<211> LENGTH: 1599
<212> TYPE: DNA
<213> ORGANISM: homo sapiens

<400> SEQUENCE: 19
atgccttggc tgctctcagc ccccaagctg gttcccgctg tagcaaacgt ccgcggcctc      60
tcaggatgta tgttgtgttc acagcgaagg tactcccttc agcctgtccc agaaaggagg     120
attccaaacc gatacttagg ccagcccagc cccttacac acccacacct cctcagacca     180
ggggaggtaa ctccaggact atctcaggtg aatatgcac ttcgcagaca caaactaatg     240
tctctgatcc agaaggaagc tcaagggcag agtgggacag accagacagt ggttgtgctc     300
tccaacccta catactacat gagcaacgat attccctata ctttccacca agacaacaat     360
ttcctgtacc tatgtggatt ccaagagcct gatagcattc ttgtccttca gagcctccct     420
ggcaaacaat taccatcaca caaagccata cttttttgtgc ctcggcgaga tcccagtcga     480
gaactttggg atggtccgcg atctggcact gatggagcaa tagctctaac tggagtagac     540
gaagcctata cgctagaaga atttcaacat cttctaccaa aaatgaaagt gctcttgcca     600
gctcttcaaa aggaggtact gttctccaag aacgatccat gcatcacagc atcagaatca     660
cctgctgaga cgaacatggt ttggtatgac tggatgaggc cctcacatgc acagcttcac     720
tctgactata tgcagcccct gactgaggcc aaagccaaga gcaagaacaa ggttcggggt     780
gttcagcagc tgatacagcg cctccggctg atcaagtctc ctgcagaaat tgaacgaatg     840
cagattgctg ggaagctgac atcacaggct ttcatagaaa ccatgttcac cagtaaagcc     900
cctgtggaag aagccttct ttatgctaag tttgaatttg aatgccgggc tcgtggcgca     960 gacatttag cctatccacc tgtggtggct ggtggtaatc ggtcaaacac tttgcactat    1020
gtgaaaaata tcaactcat caaggatggg gaaatggtgc ttctggatgg aggttgtgag    1080
tcttcctgct atgtgagtga catcacacgt acgtggccag tcaatggcag gttcaccgca    1140
cctcaggcag aactctatga agccgttcta gagatccaaa gagattgttt ggccctctgc    1200
ttccctggga caagcttgga gaacatctac agcatgatgc tgaccctgat aggacagaag    1260
```

-continued

```
cttaaagact tggggatcat gaagaacatt aaggaaaata atgccttcaa ggctgctcga    1320
aaatactgtc ctcatcatgt tggccactac ctcgggatgg atgtccatga cactccagac    1380 atgcccccgtt ccctccctct gcagcctggg atggtaatca caattgagcc cggcatttat    1440
attccagagg atgacaaaga tgccccagag aagtttcggg gtcttggtgt acgaattgag    1500
gatgatgtag tggtgactca ggactcacct ctcatccttt ctgcagactg tcccaaagag    1560
atgaatgaca ttgaacagat atgcagccag gcttcttga                          1599
```

<210> SEQ ID NO 20
<211> LENGTH: 532
<212> TYPE: PRT
<213> ORGANISM: homo sapiens

<400> SEQUENCE: 20

```
Met Pro Trp Leu Leu Ser Ala Pro Lys Leu Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Val Leu Leu Pro Ala Leu Gln Lys Glu Val Leu Phe
        195                 200                 205

Ser Lys Asn Asp Pro Cys Ile Thr Ala Ser Glu Ser Pro Ala Glu Thr
    210                 215                 220

Asn Met Val Trp Tyr Asp Trp Met Arg Pro Ser His Ala Gln Leu His
225                 230                 235                 240

Ser Asp Tyr Met Gln Pro Leu Thr Glu Ala Lys Ala Lys Ser Lys Asn
                245                 250                 255

Lys Val Arg Gly Val Gln Leu Ile Gln Arg Leu Arg Leu Ile Lys
            260                 265                 270

Ser Pro Ala Glu Ile Glu Arg Met Gln Ile Ala Gly Lys Leu Thr Ser
        275                 280                 285

Gln Ala Phe Ile Glu Thr Met Phe Thr Ser Lys Ala Pro Val Glu Glu
    290                 295                 300

Ala Phe Leu Tyr Ala Lys Phe Glu Phe Glu Cys Arg Ala Arg Gly Ala
```

-continued

```
          305                 310                 315                 320
Asp Ile Leu Ala Tyr Pro Pro Val Val Ala Gly Gly Asn Arg Ser Asn
                325                 330                 335
Thr Leu His Tyr Val Lys Asn Asn Gln Leu Ile Lys Asp Gly Glu Met
            340                 345                 350
Val Leu Leu Asp Gly Gly Cys Glu Ser Ser Cys Tyr Val Ser Asp Ile
            355                 360                 365
Thr Arg Thr Trp Pro Val Asn Gly Arg Phe Thr Ala Pro Gln Ala Glu
        370                 375                 380
Leu Tyr Glu Ala Val Leu Glu Ile Gln Arg Asp Cys Leu Ala Leu Cys
385                 390                 395                 400
Phe Pro Gly Thr Ser Leu Glu Asn Ile Tyr Ser Met Met Leu Thr Leu
                405                 410                 415
Ile Gly Gln Lys Leu Lys Asp Leu Gly Ile Met Lys Asn Ile Lys Glu
            420                 425                 430
Asn Asn Ala Phe Lys Ala Ala Arg Lys Tyr Cys Pro His His Val Gly
            435                 440                 445
His Tyr Leu Gly Met Asp Val His Asp Thr Pro Asp Met Pro Arg Ser
        450                 455                 460
Leu Pro Leu Gln Pro Gly Met Val Ile Thr Ile Glu Pro Gly Ile Tyr
465                 470                 475                 480
Ile Pro Glu Asp Asp Lys Asp Ala Pro Glu Lys Phe Arg Gly Leu Gly
                485                 490                 495
Val Arg Ile Glu Asp Asp Val Val Thr Gln Asp Ser Pro Leu Ile
            500                 505                 510
Leu Ser Ala Asp Cys Pro Lys Glu Met Asn Asp Ile Glu Gln Ile Cys
            515                 520                 525
Ser Gln Ala Ser
        530

<210> SEQ ID NO 21
<211> LENGTH: 1287
<212> TYPE: DNA
<213> ORGANISM: homo sapiens

<400> SEQUENCE: 21
atgtctctga tccagaagga agctcaaggg cagagtggga cagaccagac agtggttgtg      60
ctctccaacc ctacatacta catgagcaac gatattccct atactttcca ccaagacaac     120
aatttcctgt acctatgtgg attccaagag cctgatagca ttcttgtcct tcagagcctc     180
cctggcaaac aattaccatc acacaaagcc tactttttg tgcctcggcg agatcccagt     240
cgagaacttt gggatggtcc gcgatctggc actgatggag caatagctct aactggagta     300
gacgaagcct atacgctaga gaatttcaa catcttctac aaaaatgaa agctgagacg     360 aacatggttt ggtatgactg gatgaggccc tcacatgcac agcttcactc tgactatatg     420
cagcccctga ctgaggccaa agccaagagc aagaacaagg ttcggggtgt tcagcagctg     480
atacagcgcc tccggctgat caagtctcct gcagaaattg aacgaatgca gattgctggg     540
aagctgacat cacaggcttt catagaaacc atgttcacca gtaaagcccc tgtggaagaa     600
gcctttcttt atgctaagtt tgaatttgaa tgccgggctc gtggcgcaga catttagcc     660 tatccacctg tggtggctgg tggtaatcgg tcaaacactt tgcactatgt gaaaaataat     720
caactcatca aggatgggga aatggtgctt ctggatggag ttgtgagtc ttcctgctat     780 gtgagtgaca tcacacgtac gtggccagtc aatggcaggt tcaccgcacc tcaggcagaa     840
```

```
ctctatgaag ccgttctaga gatccaaaga gattgtttgg ccctctgctt ccctgggaca    900
agcttggaga acatctacag catgatgctg accctgatag gacagaagct taaagacttg    960
gggatcatga agaacattaa ggaaaataat gccttcaagg ctgctcgaaa atactgtcct    1020
catcatgttg ccactacct cgggatggat gtccatgaca ctccagacat gccccgttcc     1080
ctccctctgc agcctgggat ggtaatcaca attgagcccg gcatttatat tccagaggat    1140
gacaaagatg ccccagagaa gtttcggggt cttggtgtac gaattgagga tgatgtagtg    1200
gtgactcagg actcacctct catcctttct gcagactgtc ccaaagagat gaatgacatt    1260
gaacagatat gcagccaggc ttcttga                                        1287
```

<210> SEQ ID NO 22
<211> LENGTH: 428
<212> TYPE: PRT
<213> ORGANISM: homo sapiens

<400> SEQUENCE: 22

```
Met Ser Leu Ile Gln Lys Glu Ala Gln Gly Gln Ser Gly Thr Asp Gln
 1               5                  10                  15

Thr Val Val Leu Ser Asn Pro Thr Tyr Met Ser Asn Asp Ile
            20                  25                  30

Pro Tyr Thr Phe His Gln Asp Asn Asn Phe Leu Tyr Leu Cys Gly Phe
        35                  40                  45

Gln Glu Pro Asp Ser Ile Leu Val Leu Gln Ser Leu Pro Gly Lys Gln
    50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
                85                  90                  95

Leu Thr Gly Val Asp Glu Ala Tyr Thr Leu Glu Glu Phe Gln His Leu
            100                 105                 110

Leu Pro Lys Met Lys Ala Glu Thr Asn Met Val Trp Tyr Asp Trp Met
        115                 120                 125

Arg Pro Ser His Ala Gln Leu His Ser Asp Tyr Met Gln Pro Leu Thr
    130                 135                 140

Glu Ala Lys Ala Lys Ser Lys Asn Lys Val Arg Gly Val Gln Gln Leu
145                 150                 155                 160

Ile Gln Arg Leu Arg Leu Ile Lys Ser Pro Ala Glu Ile Glu Arg Met
                165                 170                 175

Gln Ile Ala Gly Lys Leu Thr Ser Gln Ala Phe Ile Glu Thr Met Phe
            180                 185                 190

Thr Ser Lys Ala Pro Val Glu Glu Ala Phe Leu Tyr Ala Lys Phe Glu
        195                 200                 205

Phe Glu Cys Arg Ala Arg Gly Ala Asp Ile Leu Ala Tyr Pro Pro Val
    210                 215                 220

Val Ala Gly Gly Asn Arg Ser Asn Thr Leu His Tyr Val Lys Asn Asn
225                 230                 235                 240

Gln Leu Ile Lys Asp Gly Glu Met Val Leu Leu Asp Gly Gly Cys Glu
                245                 250                 255

Ser Ser Cys Tyr Val Ser Asp Ile Thr Arg Thr Trp Pro Val Asn Gly
            260                 265                 270

Arg Phe Thr Ala Pro Gln Ala Glu Leu Tyr Glu Ala Val Leu Glu Ile
        275                 280                 285
```

```
                        -continued

Gln Arg Asp Cys Leu Ala Leu Cys Phe Pro Gly Thr Ser Leu Glu Asn
    290                 295                 300

Ile Tyr Ser Met Met Leu Thr Leu Ile Gly Gln Lys Leu Lys Asp Leu
305                 310                 315                 320

Gly Ile Met Lys Asn Ile Lys Glu Asn Asn Ala Phe Lys Ala Ala Arg
                325                 330                 335

Lys Tyr Cys Pro His His Val Gly His Tyr Leu Gly Met Asp Val His
            340                 345                 350

Asp Thr Pro Asp Met Pro Arg Ser Leu Pro Leu Gln Pro Gly Met Val
        355                 360                 365

Ile Thr Ile Glu Pro Gly Ile Tyr Ile Pro Glu Asp Asp Lys Asp Ala
    370                 375                 380

Pro Glu Lys Phe Arg Gly Leu Gly Val Arg Ile Glu Asp Asp Val Val
385                 390                 395                 400

Val Thr Gln Asp Ser Pro Leu Ile Leu Ser Ala Asp Cys Pro Lys Glu
                405                 410                 415

Met Asn Asp Ile Glu Gln Ile Cys Ser Gln Ala Ser
                420                 425

<210> SEQ ID NO 23
<211> LENGTH: 1530
<212> TYPE: DNA
<213> ORGANISM: homo sapiens

<400> SEQUENCE: 23
atgttgtgtt cacagcgaag gtactccctt cagcctgtcc cagaaaggag gattccaaac    60
cgatacttag gccagcccag ccccttttaca cacccacacc tcctcagacc agggaggta   120 actccaggac tatctcaggt ggaatatgca cttcgcagac acaaactaat gtctctgatc   180
cagaaggaag ctcaagggca gagtgggaca gaccagacag tggttgtgct ctccaaccct   240
acatactaca tgagcaacga tattccctat actttccacc aagacaacaa tttcctgtac   300
ctatgtggat ccaagagcc tgatagcatt cttgtccttc agagcctccc tggcaaacaa   360
ttaccatcac acaaagccat acttttttgtg cctcggcgag atcccagtcg agaactttgg   420
gatggtccgc gatctggcac tgatggagca atagctctaa ctggagtaga cgaagcctat   480
acgctagaag aatttcaaca tcttctacca aaaatgaaag tgctcttgcc agctcttcaa   540
aaggaggtac tgttctccaa gaacgatcca tgcatcacag catcagaatc acctgctgag   600
acgaacatgg tttggtatga ctggatgagg ccctcacatg cacagcttca ctctgactat   660
atgcagcccc tgactgaggc aaagccaag agcaagaaca aggttcgggg tgttcagcag   720
ctgatacagc gcctccggct gatcaagtct cctgcagaaa ttgaacgaat gcagattgct   780
gggaagctga catcacaggc tttcatagaa accatgttca ccagtaaagc ccctgtggaa   840
gaagcctttc tttatgctaa gtttgaattt gaatgccggg ctcgtggcgc agacatttta   900
gcctatccac ctgtggtggc tggtggtaat cggtcaaaca ctttgcacta tgtgaaaaat   960
aatcaactca tcaaggatgg ggaaatggtg cttctggatg gaggttgtga gtcttcctgc  1020
tatgtgagtg acatcacacg tacgtggcca gtcaatggca ggttcaccgc acctcaggca  1080
gaactctatg aagccgttct agagatccaa agagattgtt tggccctctg cttccctggg  1140
acaagcttgg agaacatcta cagcatgatg ctgaccctga ggacagaa gcttaaagac  1200 ttggggatca tgaagaacat taaggaaaat aatgccttca aggctgctcg aaaatactgt  1260
cctcatcatg ttggccacta cctcgggatg gatgtccatg acactccaga catgccccgt  1320
```

```
tccctccctc tgcagcctgg gatggtaatc acaattgagc ccggcattta tattccagag    1380
gatgacaaag atgccccaga aagtttcgg ggtcttggtg tacgaattga ggatgatgta    1440
gtggtgactc aggactcacc tctcatcctt tctgcagact gtcccaaaga gatgaatgac    1500
attgaacaga tatgcagcca ggcttcttga                                      1530
```

<210> SEQ ID NO 24
<211> LENGTH: 509
<212> TYPE: PRT
<213> ORGANISM: homo sapiens

<400> SEQUENCE: 24

```
Met Leu Cys Ser Gln Arg Arg Tyr Ser Leu Gln Pro Val Pro Glu Arg
 1               5                  10                  15

Arg Ile Pro Asn Arg Tyr Leu Gly Gln Pro Ser Pro Phe Thr His Pro
                20                  25                  30

His Leu Leu Arg Pro Gly Glu Val Thr Pro Gly Leu Ser Gln Val Glu
            35                  40                  45

Tyr Ala Leu Arg Arg His Lys Leu Met Ser Leu Ile Gln Lys Glu Ala
        50                  55                  60

Gln Gly Gln Ser Gly Thr Asp Gln Thr Val Val Val Leu Ser Asn Pro
 65                  70                  75                  80

Thr Tyr Tyr Met Ser Asn Asp Ile Pro Tyr Thr Phe His Gln Asp Asn
                 85                  90                  95

Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125

Phe Val Pro Arg Arg Asp Pro Ser Arg Glu Leu Trp Asp Gly Pro Arg
130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Val Leu Leu
                165                 170                 175

Pro Ala Leu Gln Lys Glu Val Leu Phe Ser Lys Asn Asp Pro Cys Ile
            180                 185                 190

Thr Ala Ser Glu Ser Pro Ala Glu Thr Asn Met Val Trp Tyr Asp Trp
        195                 200                 205

Met Arg Pro Ser His Ala Gln Leu His Ser Asp Tyr Met Gln Pro Leu
210                 215                 220

Thr Glu Ala Lys Ala Lys Ser Lys Asn Lys Val Arg Gly Val Gln Gln
225                 230                 235                 240

Leu Ile Gln Arg Leu Arg Leu Ile Lys Ser Pro Ala Glu Ile Glu Arg
                245                 250                 255

Met Gln Ile Ala Gly Lys Leu Thr Ser Gln Ala Phe Ile Glu Thr Met
            260                 265                 270

Phe Thr Ser Lys Ala Pro Val Glu Glu Ala Phe Leu Tyr Ala Lys Phe
        275                 280                 285

Glu Phe Glu Cys Arg Ala Arg Gly Ala Asp Ile Leu Ala Tyr Pro Pro
290                 295                 300

Val Val Ala Gly Gly Asn Arg Ser Asn Thr Leu His Tyr Val Lys Asn
305                 310                 315                 320

Asn Gln Leu Ile Lys Asp Gly Glu Met Val Leu Leu Asp Gly Gly Cys
                325                 330                 335
```

```
Glu Ser Ser Cys Tyr Val Ser Asp Ile Thr Arg Thr Trp Pro Val Asn
                340                 345                 350
Gly Arg Phe Thr Ala Pro Gln Ala Glu Leu Tyr Glu Ala Val Leu Glu
            355                 360                 365
Ile Gln Arg Asp Cys Leu Ala Leu Cys Phe Pro Gly Thr Ser Leu Glu
        370                 375                 380
Asn Ile Tyr Ser Met Met Leu Thr Leu Ile Gly Gln Lys Leu Lys Asp
385                 390                 395                 400
Leu Gly Ile Met Lys Asn Ile Lys Glu Asn Asn Ala Phe Lys Ala Ala
                405                 410                 415
Arg Lys Tyr Cys Pro His His Val Gly His Tyr Leu Gly Met Asp Val
            420                 425                 430
His Asp Thr Pro Asp Met Pro Arg Ser Leu Pro Leu Gln Pro Gly Met
        435                 440                 445
Val Ile Thr Ile Glu Pro Gly Ile Tyr Ile Pro Glu Asp Asp Lys Asp
    450                 455                 460
Ala Pro Glu Lys Phe Arg Gly Leu Gly Val Arg Ile Glu Asp Asp Val
465                 470                 475                 480
Val Val Thr Gln Asp Ser Pro Leu Ile Leu Ser Ala Asp Cys Pro Lys
                485                 490                 495
Glu Met Asn Asp Ile Glu Gln Ile Cys Ser Gln Ala Ser
                500                 505
```

<210> SEQ ID NO 25
<211> LENGTH: 1455
<212> TYPE: DNA
<213> ORGANISM: homo sapiens

<400> SEQUENCE: 25

```
atgttgtgtt cacagcgaag gtactcccct cagcctgtcc cagaaaggag gattccaaac      60
cgatacttag gccagcccag ccccttaca  cacccacacc tcctcagacc aggggaggta     120
actccaggac tatctcaggt ggaatatgca cttcgcagac acaaactaat gtctctgatc     180
cagaaggaag ctcaagggca gagtgggaca gaccagacag tggttgtgct ctccaaccct     240
acatactaca tgagcaacga tattcccctat actttccacc aagacaacaa tttcctgtac    300
ctatgtggat ccaagagcc  tgatagcatt cttgtccttc agagcctccc tgcaaacaa      360
ttaccatcac acaaagccat acttttttgtg cctcggcgag atcccagtcg agaactttgg    420
gatggtccgc gatctggcac tgatggagca atagctctaa ctggagtaga cgaagcctat    480
acgctagaag aatttcaaca tcttctacca aaaatgaaag ctgagacgaa catggtttgg    540
tatgactgga tgaggccctc acatgcacag cttcactctg actatatgca gccccctgact   600
gaggccaaag ccaagagcaa gaacaaggtt cggggtgttc agcagctgat acagcgcctc    660
cggctgatca gtctcctgc agaaattgaa cgaatgcaga ttgctgggaa gctgacatca    720
caggctttca tagaaaccat gttcaccagt aaagcccctg tggaagaagc ctttctttat    780
gctaagtttg aatttgaatg ccgggctcgt ggcgcagaca ttttagccta tccacctgtg    840
gtggctggtg gtaatcggtc aaacactttg cactatgtga aaaataatca actcatcaag    900
gatggggaaa tggtgcttct ggatggaggt tgtgagtctt cctgctatgt gagtgacatc    960
acacgtacgt ggccagtcaa tggcaggttc accgcacctc aggcagaact ctatgaagcc   1020
gttctagaga tccaaagaga ttgtttggcc ctctgcttcc ctgggacaag cttggagaac   1080
atctacagca tgatgctgac cctgatagga cagaagctta aagactttggg gatcatgaag   1140
```

-continued

```
aacattaagg aaaataatgc cttcaaggct gctcgaaaat actgtcctca tcatgttggc      1200
cactacctcg ggatggatgt ccatgacact ccagacatgc cccgttccct ccctctgcag      1260
cctgggatgg taatcacaat tgagcccggc atttatattc cagaggatga caaagatgcc      1320
ccagagaagt ttcggggtct tggtgtacga attgaggatg atgtagtggt gactcaggac      1380
tcacctctca tcctttctgc agactgtccc aaagagatga atgacattga acagatatgc      1440
agccaggctt cttga                                                       1455
```

<210> SEQ ID NO 26
<211> LENGTH: 484
<212> TYPE: PRT
<213> ORGANISM: homo sapiens

<400> SEQUENCE: 26

```
Met Leu Cys Ser Gln Arg Arg Tyr Ser Leu Gln Pro Val Pro Glu Arg
  1               5                  10                  15

Arg Ile Pro Asn Arg Tyr Leu Gly Gln Pro Ser Pro Phe Thr His Pro
                 20                  25                  30

His Leu Leu Arg Pro Gly Glu Val Thr Pro Gly Leu Ser Gln Val Glu
             35                  40                  45

Tyr Ala Leu Arg Arg His Lys Leu Met Ser Leu Ile Gln Lys Glu Ala
         50                  55                  60

Gln Gly Gln Ser Gly Thr Asp Gln Thr Val Val Leu Ser Asn Pro
 65                  70                  75                  80

Thr Tyr Tyr Met Ser Asn Asp Ile Pro Tyr Thr Phe His Gln Asp Asn
                 85                  90                  95

Asn Phe Leu Tyr Leu Cys Gly Phe Gln Glu Pro Asp Ser Ile Leu Val
                100                 105                 110

Leu Gln Ser Leu Pro Gly Lys Gln Leu Pro Ser His Lys Ala Ile Leu
            115                 120                 125

Phe Val Pro Arg Arg Asp Pro Ser Arg Glu Leu Trp Asp Gly Pro Arg
        130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Ala Glu Thr
                165                 170                 175

Asn Met Val Trp Tyr Asp Trp Met Arg Pro Ser His Ala Gln Leu His
            180                 185                 190

Ser Asp Tyr Met Gln Pro Leu Thr Glu Ala Lys Ala Lys Ser Lys Asn
        195                 200                 205

Lys Val Arg Gly Val Gln Gln Leu Ile Gln Arg Leu Arg Leu Ile Lys
    210                 215                 220

Ser Pro Ala Glu Ile Glu Arg Met Gln Ile Ala Gly Lys Leu Thr Ser
225                 230                 235                 240

Gln Ala Phe Ile Glu Thr Met Phe Thr Ser Lys Ala Pro Val Glu Glu
                245                 250                 255

Ala Phe Leu Tyr Ala Lys Phe Glu Phe Glu Cys Arg Ala Arg Gly Ala
            260                 265                 270

Asp Ile Leu Ala Tyr Pro Pro Val Val Ala Gly Gly Asn Arg Ser Asn
        275                 280                 285

Thr Leu His Tyr Val Lys Asn Asn Gln Leu Ile Lys Asp Gly Glu Met
    290                 295                 300

Val Leu Leu Asp Gly Gly Cys Glu Ser Ser Cys Tyr Val Ser Asp Ile
305                 310                 315                 320
```

```
Thr Arg Thr Trp Pro Val Asn Gly Arg Phe Thr Ala Pro Gln Ala Glu
                325                 330                 335

Leu Tyr Glu Ala Val Leu Glu Ile Gln Arg Asp Cys Leu Ala Leu Cys
            340                 345                 350

Phe Pro Gly Thr Ser Leu Glu Asn Ile Tyr Ser Met Met Leu Thr Leu
        355                 360                 365

Ile Gly Gln Lys Leu Lys Asp Leu Gly Ile Met Lys Asn Ile Lys Glu
    370                 375                 380

Asn Asn Ala Phe Lys Ala Ala Arg Lys Tyr Cys Pro His His Val Gly
385                 390                 395                 400

His Tyr Leu Gly Met Asp Val His Asp Thr Pro Asp Met Pro Arg Ser
                405                 410                 415

Leu Pro Leu Gln Pro Gly Met Val Ile Thr Ile Glu Pro Gly Ile Tyr
            420                 425                 430

Ile Pro Glu Asp Asp Lys Asp Ala Pro Glu Lys Phe Arg Gly Leu Gly
        435                 440                 445

Val Arg Ile Glu Asp Asp Val Val Thr Gln Asp Ser Pro Leu Ile
    450                 455                 460

Leu Ser Ala Asp Cys Pro Lys Glu Met Asn Asp Ile Glu Gln Ile Cys
465                 470                 475                 480

Ser Gln Ala Ser

<210> SEQ ID NO 27
<211> LENGTH: 3208
<212> TYPE: DNA
<213> ORGANISM: homo sapiens

<400> SEQUENCE: 27
gcggccctgc aggcggttgc gttccccgtc gttaccctct ttctcttccc gacgcgtgag     60
ttaggccgta atgccttggc tgctctcagc ccccaagctg gttcccgctg tagcaaacgt    120
ccgcggcctc tcagtcctga atcctctgga ctgtttcccc tgtatgtttc cctggaagct    180
tcaggcagtg cctcataagc caatggaatc tgttgctaat agccacagca tatcccttgc    240
ataatatgac ctctagatta ctgcgcctta attgcttccc agctcttcta tgctttggtt    300
tagaaaaatg aagtactgac ttacgggtga agaaagtatt caaacagttg acatatttat    360
ttcagtcaag aaacagttca gagggagata caaacaagta acttagttac aatataatag    420
ttatgatgag aggaagtact ggatgctaaa caattatatg agagacagct caggctgggg    480
gtgtcaatga agcctcttg gaggaagtag cctgatatgt taactttctg catgccagtg    540
aagacactat gtgtgcatga gtacgtgtgc acgagcgtgc atgtggagaa ggtgcaggag    600
gagagaaaga gaaatcacca atgcaacagc agcctactcc accagtgggt tagtgctgct    660
ggagggagat gaaagatta ggaaggatgt atgttgtgtt cacagcgaag gtactccctt    720
cagcctgtcc cagaaaggag gattccaaac cgatacttag gccagcccag cccctttaca    780
cacccacacc tcctcagacc agactcgaat tcctgctggg aagtcggctg aaactaagga    840
aatgcagctc accactgaaa cccacaagaa atcagagttt tcaaagctg taaggggagg     900
taactccagg actatctcag gtggaatatg cacttcgcag acacaaacta atgtctctga    960
tccagaagga agctcaaggg cagagtggga cagaccagac agtggttgtg ctctccaacc   1020
ctacatacta catgagcaac gatattccct atactttcca ccaagacaac aatttcctgt   1080
acctatgtgg attccaagag cctgatagca ttcttgtcct tcagagcctc cctggcaaac   1140
```

-continued

```
aattaccatc acacaaagcc atacttttg tgcctcggcg agatcccagt cgagaacttt    1200
gggatggtcc gcgatctggc actgatggag caatagctct aactggagta gacgaagcct    1260
atacgctaga agaatttcaa catcttctac caaaaatgaa agtgctcttg ccagctcttc    1320
aaaaggaggt actgttctcc aagaacgatc catgcatcac agcatcagaa tcacctgctg    1380
agacgaacat ggtttggtat gactggatga ggccctcaca tgcacagctt cactctgact    1440
atatgcagcc cctgactgag gccaaagcca agagcaagaa caaggttcgg ggtgttcagc    1500
agctgataca gcgcctccgg ctgatcaagt ctcctgcaga aattgaacga atgcagattg    1560
ctgggaagct gacatcacag gtatgattcc tattgaaaag tttttccag ccgggcgcgg    1620
tggctcacgc ctgtaatcca agcactttgg gaggccgagg caggtggatc atgaggtcag    1680
gagatcgaga ccatcctggc taacatggtg aaacccgtc tctactaaaa aaacataaaa    1740
aattagccgg gcatggtggc gggctcctgt agtcccagct actcggtagg ctgaggcagg    1800
agaatggtgt gaacccggga ggcagagctt gcagtgagcc gagatcgggc cactgcactc    1860
cagcctggcg acagacgaga ttcatcttaa aaaaaaaaa aaaaaaaact ttcatagaaa    1920
ccatgttcac cagtaaagcc cctgtggaag aagcctttct ttatgctaag tttgaatttg    1980
aatgccgggc tcgtggcgca gacattttag cctatccacc tgtggtggct ggtggtaatc    2040
ggtcaaacac tttgcactat gtgaaaaata atcaactcat caaggatggg gaaatggtgc    2100
ttctggatgg aggttgtgag tcttcctgct atgtgagtga catcacacgt acgtggccag    2160
tcaatggcag gttcaccgca cctcaggcag aactctatga agccgttcta gagatccaaa    2220
gagattgttt ggccctctgc ttccctggga caagcttgga gaacatctac agcatgatgc    2280
tgaccctgat aggacagaag cttaaagact tggggatcat gaagaacatt aaggaaaata    2340
atgccttcaa ggctgctcga aaatactgtc ctcatcatgt tggccactac ctcgggatgg    2400
atgtccatga cactccagac atgccccgtt ccctccctct gcagcctggg atggtaatca    2460
caattgagcc cggcatttat attccagagg atgacaaaga tgccccagag aagtttcggg    2520
gtcttggtgt acgaattgag gatgatgtag tggtgactca ggactcacct ctcatccttt    2580
ctgcagactg tcccaaagag atgaatgaca ttgaacagat atgcagccag gcttcttgac    2640
cttcactgcg gcccacatgc acctcaggtt caaaatgggt gtcttctggc agccctgcac    2700
gtgtgctttc tgagtgtctc tgtgtgtgca ttaatatatg cattccatt gggagcataa    2760
aaaaaaaaaa aaaaatggaa tgcagtagcc ctctgggcct gggatattgt ggttgataac    2820
tgtgccatct gcaggaacca cattatggat ctttgcatag aatgtcaagc taaccaggcg    2880
tccgctactt cagaagagtg tactgtcgca tggggagtct gtaaccatgc ttttcacttc    2940
cactgcatct ctcgctggct caaaacacga caggtgtgtc cattggacaa cagagagtgg    3000
gaattccaaa agtatgggca ctaggaaaag acttcttcca tcaagcttaa ttgttttgtt    3060
attcatttaa tgactttccc tgctgttacc taattacaaa ttggatggaa ctgtgttttt    3120
ttctgctttg ttttttcagt ttgctgtttc tgtagccata ttggattctg tgtcaaataa    3180
agtccagttg gattctggaa aaaaaaa                                         3208
```

HUMAN PROTEASES AND POLYNUCLEOTIDES ENCODING THE SAME

The present application is a divisional of U.S. application Ser. No. 10/214,811, filed Aug. 7, 2002 now issued as U.S. Pat. No. 6,743,626, which is a continuation of U.S. application Ser. No. 09/780,016, filed Feb. 9, 2001, which issued as U.S. Pat. No. 6,509,456 on Jan. 21, 2003, which claims the benefit of U.S. Provisional Application No. 60/181,924 which was filed on Feb. 11, 2000, each of which are herein incorporated by reference in their entirety.

1. INTRODUCTION

The present invention relates to the discovery, identification, and characterization of novel human polynucleotides encoding proteins sharing sequence similarity with mammalian proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring, the treatment of physiological disorders or infectious disease.

2. BACKGROUND OF THE INVENTION

Proteases cleave protein substrates as part of degradation, maturation, and secretary pathways within the body. Proteases have been associated with, inter alia, regulating development, diabetes, obesity, infertility, modulating cellular processes, and infectious disease.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal proteases, and particularly aminopeptidases.

The novel human nucleic acid (cDNA) sequences described herein, encode proteins/open reading frames (ORFs) of 507, 69, 290, 265, 211, 267, 186, 242, 453, 532, 428, 509, and 484 amino acids in length (see SEQ ID NOS: 2, 4, 6, 8, 10, 12, 14, 16, 18, 20, 22, 24, and 26 respectively).

The invention also encompasses agonists and antagonists of the described NHPs, including small molecules, large molecules, mutant NHPs, or portions thereof that compete with native NHPs, NHP peptides, and NHP antibodies, as well as nucleotide sequences that can be used to inhibit the expression of the described NHPs (e.g., antisense and ribozyme molecules, and gene or regulatory sequence replacement constructs) or to enhance the expression of the described NHPs (e.g., expression constructs that place the described sequence under the control of a strong promoter system), and transgenic animals that express a NHP transgene, or "knockout" animals (which can be conditional) that do not express a functional NHP. A gene trapped "knockout" murine ES cell line has been produced that mutates a murine homolog of the described NHPs. Accordingly, an additional aspect of the present invention includes a knockout mouse that is characterized by reduced levels of NHP expression.

Further, the present invention also relates to processes for identifying compounds that modulate, i.e., act as agonists or antagonists, of NHP expression and/or NHP activity that utilize purified preparations of the described NHP and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences. SEQ ID NO:27 describes a NHP ORF with flanking sequences.

5. DETAILED DESCRIPTION OF THE INVENTION

The NHPs, described for the first time herein, are novel proteins that are expressed in, inter alia, human cell lines, and human fetal brain, brain, pituitary, cerebellum, spinal cord, thymus, spleen, lymph node, bone marrow, trachea, kidney, fetal liver, liver, prostate, testis, thyroid, adrenal gland, pancreas, salivary gland, stomach, small intestine, colon, uterus, placenta, mammary gland, adipose, skin, esophagus, bladder, cervix, rectum, pericardium, hypothalamus, ovary, fetal kidney, and fetal lung cells.

The described NHPs share sequence similarity with aminopeptidases, and particularly aminopeptidase P, from a variety of organisms. Aminopeptidases have been implicated in a variety cellular and disease processes and have been subject to considerable scientific scrutiny. For example, U.S. Pat. No. 5,972,680 describes uses and applications for proteases such as the presently described NHPs and U.S. Pat. No. 5,656,603 describes a variety of chemical antagonists of aminopeptidase P, both of which are herein incorporated by reference in their entirety.

The described sequences were compiled from gene trapped cDNAs and clones isolated from a human testis cDNA library (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of a NHP that correspond to functional domains of the NHP, and the polypeptide products specified by such nucleotide sequences, including but not limited to the novel regions of any active domain(s); (c) isolated nucleotides that encode mutant versions, engineered or naturally occurring, of a described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds. 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–27 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–27, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays-comprising sequences first disclosed in SEQ ID NOS:1–27 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–27.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–27 provides detailed information about transcriptional changes involved in a specific pathway, potentially leading to the identification of novel components or gene functions that manifest themselves as novel phenotypes.

Probes consisting of sequences first disclosed in SEQ ID NOS:1–27 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–27 can be utilized in microarrays or other assay formats, to screen collections of genetic material from patients who have a particular medical condition. These investigations can also be carried out using the sequences first disclosed in SEQ ID. NOS:1–27 in silico and by comparing previously collected genetic databases and the disclosed sequences using computer software known to those in the art.

Thus the sequences first disclosed in SEQ ID NOS:1–27 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–27. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2, 6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or-tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, .following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a. NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize an endogenous NHP receptor, accessory molecule, or substrate. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozye molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHP are presented in the Sequence Listing. SEQ ID NO:27 describes a NHP ORF as well as flanking regions. The NHP nucleotides were obtained from human cDNA libraries using probes and/or primers generated from human gene-trapped sequence tags. Expression analysis has provided evidence that the described NHPs are widely expressed in both human tissues as well as gene trapped human cells.

5.2 NHPs and NHP Polypeptides

NHPs, NHP polypeptides, NHP peptide fragments, mutated, truncated, or deleted forms of NHP, and/or NHP fusion proteins can be prepared for a variety of uses. These uses include, but are not limited to, the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequence encoded by the described NHP polynucleotides. The NHPs display initiator methionines in DNA sequence contexts consistent with a translation initiation site, and display a consensus signal sequence characteristic of secreted proteins.

The NHP amino acid sequences of the invention include the amino acid sequences presented in the Sequence Listing as well as analogues and derivatives thereof, as well as any oligopeptide sequence of at least about 10–40, generally about 12–35, or about 16–30 amino acids in length first disclosed in the Sequence Listing. Further, corresponding NHP homologues from other species are encompassed by the invention. In fact, any NHP encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4–1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP products or NHP polypeptides are thought to be soluble or secreted molecules, the peptide or polypeptide can be recovered from the culture media. Such expression systems also encompass engineered host cells that express a NHP, or a functional equivalent, in situ. Purification or enrichment of NHP from such expression systems can be accomplished using appropriate detergents and lipid micelles and methods well known to those skilled in the art. However, such engineered host cells themselve's may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced;.pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus. (AcNPV) is used as a vector to express foreign sequences. The virus grows in Spodoptera frugiperda cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinacebus coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific. initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavages of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a Delectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻or aprt⁻cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid:(Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell.

Alternatively targeting of NHP or its nucleic acid sequence might be achieved using liposome or lipid complex based delivery systems. Such technologies are described in *Liposomes: A Practical Approach*, New RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for example's of such transducing sequences) to facilitate passage across cellular membranes and can optionally be engineered to include nuclear localization sequences.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated polypeptide comprising the amino acid sequence of SEQ ID NO:2.

* * * * *